United States Patent [19]

Gustafson et al.

[11] Patent Number: 5,359,134
[45] Date of Patent: Oct. 25, 1994

[54] PROCESS FOR PREPARING PHENYLTEREPHTHALIC ACID

[75] Inventors: Bruce L. Gustafson; Charles E. Sumner, Jr.; Michael Bellas, all of Kingsport; Gether Irick, Jr., Gray; Dewey W. Fuller, Jr., Bristol; Ernest W. Arnold, Blountville, all of Tenn.; Eric J. Fugate, Gate City, Va.

[73] Assignee: Eastman Chemical Company, Kingsport, Tenn.

[21] Appl. No.: 930,887

[22] Filed: Aug. 14, 1992

[51] Int. Cl.$^5$ ............................ C07C 51/265
[52] U.S. Cl. .................. 562/416; 562/487; 585/446
[58] Field of Search ............... 562/416, 487, 488; 585/400, 446

[56] References Cited

U.S. PATENT DOCUMENTS

| | | | |
|---|---|---|---|
| 3,265,762 | 8/1966 | Quisenberry | 528/176 |
| 3,354,202 | 11/1967 | Zimmerschied et al. | 562/416 X |
| 3,365,425 | 1/1968 | Watson | 528/176 |
| 4,197,412 | 4/1980 | Kimura et al. | 562/416 |
| 4,294,955 | 10/1981 | Harris, Jr. | 528/176 |
| 4,895,978 | 1/1990 | Darin et al. | 562/416 |

OTHER PUBLICATIONS

D. Bodroux, *Ann. Chim.*, 11, pp. 511–582 (1929).
Nicolescu et al., *Izvest. Akad. Nank S.S.S.R. Otdel Khim Nauk*; (1960), pp. 94–97.
Hickinbottom et al., *J. Chem. Soc.* (1957), pp. 4124–4130.
Weisburger et al., *J. Org. Chem.*, 23, 1193–1198, (1958).
STN International, Chemical Abstracts, vol. 77, No. 17, 23 Oct. 1972 (Columbus, Ohio US), J. Ratusky: "Transcarboxylations of salts of organic acids. XVIII. Anomalous course of transcarboxylations of salts of biphenylcarboxylic acids", abstract No. 113988m, & Collect. Czech. Chem. Commun., 37(7), 2436–50.
STN International, Chemical Abstracts, vol. 114, No. 4, 28 Jan. 1991 (Columbus, Ohio, US), H. T. Land et al: "Synthesis of aryl-substituted monomers for high performance polymers", abstract No. 24626g, & Makromol. Chem., 191(9), 2005–16.
STN International, Chemical Abstracts, vol. 86, No. 19, 9 May 1977 (Columbus, Ohio, US), T. A. Pashaev et al: "Study of the isomeric composition of products of the cyclopentylation and cyclohexylation of aromatic hydrocarbons", abstract No. 139512n, & Azerb. Khim. Zh., (3), 30–4.

*Primary Examiner*—José G. Dees
*Assistant Examiner*—Samuel Barts
*Attorney, Agent, or Firm*—Bernard J. Graves, Jr.

[57] ABSTRACT

Provided is a facile three step process for preparing 2-phenylterephthalic acid starting with p-xylene, followed by alkylation, dehydrogenation, and oxidation of the methyl groups corresponding to the origional p-xylene. The product, 2-phenylterephthalic acid, is useful as an intermediate in the synthesis of polyesters comprised of residues of 2-phenylterephthalic acid.

12 Claims, No Drawings

PROCESS FOR PREPARING PHENYLTEREPHTHALIC ACID

FIELD OF THE INVENTION

This invention belongs to the field of synthetic organic chemistry. More particularly, it relates to a process for preparing phenylterephthalic acid, an intermediate in the synthesis of useful polyesters.

BACKGROUND OF THE INVENTION

Phenylterephthalic acid is valuable as an interemediate in the preparation of liquid crystalline polyesters. For example, U.S. Pat. No. 4,391,966 describes the use of phenylterephthalic acid in preparing melt-spinnable, anisotropic melt forming aromatic polyesters. Further, E. K. Weisburger and J. H. Weisburger describe the reaction of 2,5-xylylmagnesium bromide with either cyclohexanone or 3-bromocyclohexene to provide 1-(2,5-xylyl)cyclohexene, which is then dehydrogenated using sulfur to provide 2,5-dimethylbiphenyl, which is oxidized by KMnO$_4$ to provide phenylterephthalic acid in 74% yield. The permangenate process provides an isolation and purification problem, since a relatively large amount of manganese waste is produced.

SUMMARY OF THE INVENTION

The present invention provides a three step process for preparing 2-phenylterephthalic acid starting with p-xylene, followed by alkylation, dehydrogenation, and oxidation of the methyl groups corresponding to the origional p-xylene.

DETAILED DESCRIPTION OF THE INVENTION

The present invention provides a process for preparing a compound of Formula (1),

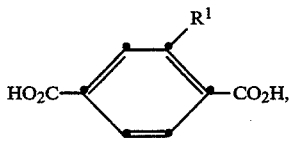

wherein R$^1$ is phenyl, which comprises the steps
(a) alkylating a compound of the formula

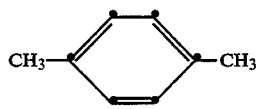

with cyclohexene in the presence of an acid catalyst to provide a compound of Formula (1),

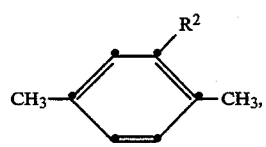

wherein R$^2$ is cyclohexyl; followed by
(b) dehydrogenation; and
(c) oxidation in the presence of air or oxygen and a cobaltous bromide oxidation catalyst system, at a temperature of about 75° C. to 250° C., and at a pressure of about 10 to 1000 psig.

In the experimental section below, it is noted that monoalkylation and dialkylation occurs thereby resulting in a mixture that may be easily purified by conventional physical separation methodology, e.g., distillation, extraction, crystallization, etc.

In the alkylation step, p-xylene is reacted with cyclohexene (or generated in situ with cyclohexanol) in the presence of an acidic catalyst. In this context, p-xylene is normally used as both reactant as well as solvent. Unreacted p-xylene can be readily recovered and recycled. The reaction will yield a mixture of mono- and di-alkylated product. If more dialkylated product is desired, a molar excess of cyclohexene should be utilized.

Reaction conditions employed for the alkylations can vary within wide ranges. The alkylation reaction can, therefore, be carried out over a wide range of temperatures, reactions times, and the like. Preferably employed are reaction temperatures in the range of 0° up to 300° C., with reaction pressures in the range of about 0.01 up to 30 atmospheres, and contact times in the range of about 0.01 up to 30 hours being especially preferred.

Preferred reaction conditions for the alkylation step will vary as a function of the starting materials employed, the acid catalyst used, the catalyst/substrate ratio, desired conversion levels, and the like. Thus, for example, with cyclohexanol as one of the starting materials, preferred reaction temperature falls within the range of 100° up to 150° C. When cyclohexene is employed as one of the starting materials, preferred reaction temperature falls within the range of 75° up to about 150° C.

Numerous acids which are suitable for catalyzing the alkylation reaction. For example, acids such as the following are useful: phosphoric acid, sulfuric acid, methanesulfonic acid, trifluoromethanesulfonic acid, polyphosphoric acid, acidic molecular sieves, SiO$_2$/Al$_2$O$_3$, p-toluenesulfonic acid, trichloroacetic acid, dichloroacetic acid, trifluoroacetic acid, aluminum trichloride, aluminum tribromide, boron trifluoride, and acidic polymers resins, such as, for example, AMBERLYST TM 15, and AEROCAT TM. Preferred for ease of handling, workup, etc., are the acidic polymeric resins such as, for example, AMBERLYST TM 15 and AEROCAT TM.

Either crystalline or amorphous SiO$_2$/Al$_2$O$_3$ catalysts may be used. Preferred catalysts include medium and large pore size silica/alumina catalysts such as the hydrogen form Y type zeolite catalysts. These zeolite catalysts are noncorrosive.

Following alkylation, the intermediate product (cyclohexyl xylene) may be recovered by conventional techniques such as, for example, extraction, distillation and the like.

The dehydrogenation of the cyclohexyl-p-xylene intermediate to produce dimethylbiphenyl can be carried out under a wide variety of conditions, preferably in the presence of a dehydrogenation catalyst. It is expected that any catalyst (or reaction conditions) which is operable for the conversion of cyclohexane or cyclohexene to benzene will be suitable for use in the practice of the present invention, although it is recognized by those of skill in the art that other catalysts and/or reaction conditions will also be suitable. Examples of dehydrogenation catalysts useful in the practice of the present invention include Group B and Group 1B metals, as well as such metals containing additional modifying components such as elemental sulfur, alkali metals and the early transition metals (i.e., Group IVA, V, VIA, and VIIA metals). Preferred modifiers include sulfur and copper. Among the preferred catalysts are the noble metals. For ease of catalyst handling and to minimize catalyst expense, it is also preferred that a supported catalyst be utilized. A presently preferred catalyst support is carbon. These dehydrogenation reactions may be conducted in fixed bed or in slurry systems.

Examples of the presently preferred dehydrogenation catalysts for use in the practice of the present invention include sulfided palladium on alumina, sulfided palladium on carbon, sulfided platinum on carbon, palladium-copper on carbon support, palladium on alumina, platinum on alumina, modified Pt/Pd on carbon or alumina and the like.

Reaction conditions for the dehydrogenation step can vary over a wide range. For example, a reaction temperature in the range of about 100° up to 500° C. is generally preferable, as is a reaction pressure in the range of about 0.01 up to 30 atmospheres, with contact times in the range of about 0.01 up to 36 hours. Further preferred reaction parameters comprise a temperature in the range of about 225° up to 350° C., pressure in the range of 0.1 up to 1 atmosphere, and contact time in the range of about 0.01 up to 24 hours.

When dehydrogenation catalyst is employed, the dehydrogenation reaction can be conducted in either batch or continuous mode. When carried out in batch mode, the substrate to catalyst weight ratio employed typically falls within the range of about 10:1 up to 1000:1, with a substrate to catalyst weight ratio of about 20:1 up to 100:1 being preferred.

When carried out in a continuous mode, the substrate to catalyst weight ratio will vary as a function of reactant space velocity, catalyst loading level, reactor design, and the like.

The use of solvent in the dehydrogenation step is optional. When employed, solvents which are stable under the dehydrogenation conditions are suitable, and are employed in amounts ranging from 10 up to 90 weight percent of the reaction mixture. Examples of suitable solvents include biphenyl, naphthalene, diphenylether, tetralin, durene, prehnitene or 1,2,3,4-tetramethylbenzene, and the like.

The catalyst utilized may be recycled from the slurry by filtering the hot reaction mixture. The filtration may be conducted at the reaction temperature, above the melting point of the reaction mixture or at a temperature between about 100° C. and 200° C. A preferred range of temperatures for recovering the catalyst by filtration is between 125° C. and 150° C.

In a preferred embodiment of the invention, hydrogen gas produced as a result of the reaction is removed from the reaction atmosphere as the reaction proceeds. This can be accomplished by a variety of techniques as are well known by those of ordinary skill in the art. For example, the removal of hydrogen gas can be attained by circulating an inert gas through the atmosphere immediately above, or directly into, the reaction mixture. By means of example, the inert gas may be nitrogen. However, other unreactive gases may also be utilized for the removal of the hydrogen gas. As one alternative, hydrogen gas can be removed by careful addition of a purge gas containing small amounts of a reactive gas, e.g., oxygen, which enables the removal of hydrogen as water.

The net result of hydrogen gas removal is to shift the equilibrium concentration from the starting material or substrate to the product of the reaction by removing from the system any amount of hydrogen produced.

Following dehydrogenation, the desired dimethyl biphenyl product (or 2-phenyl-p-xylene) can be recovered by conventional techniques, such as, for example, by crystallization, extract, distillation, precipitation and the like.

In a preferred embodiment of the present invention; the alkylation stage and the dehydrogenation stage can be integrated in such a fashion that by-product streams from the alkylation and dehydrogenation stages can be recovered and recycled for conversion to additional quantities of desired products. In this manner, di- and tri-substituted p--xylene derivatives can be returned to the alkylation stage where they are disproportionated into additional quantities of the desired mono-alkylated product. Similarly, unrelated cyclohexyl-p--xylene can be recycled to the dehydrogenation stage and subjected to additional treatment under dehydrogenation conditions.

Dimethylbiphenyl is readily oxidized to phenylterephthalic acid in the presence of air or oxygen using selected catalysts. These oxidations are generally conducted at temperatures in the range of about 75 to about 250° C. with the preferred range being about 90 to 150° C. Air pressures of about 10 to about 1000 psig are useful with 150-300 psig air being preferred.

The oxidation reactions are preferably conducted in low molecular weight aliphatic acids such as acetic, propionic, butyric acid and the like. Acetic acid is a preferred solvent and generally about 10 to 90% of the reaction charge is solvent.

Highly useful catalysts for this oxidation process include those based on a cobaltous/manganous/bromide system. Zirconium compounds may be used instead of the manganese moiety if desired or only cobaltous/bromide can be used. Useful forms of these catalyst components include the organic acid salts of the metals such as cobalt acetate, cobalt propionate, cobalt butyrate, cobalt benzoate, cobalt toluate or the corresponding manganese or zirconium salts and the like. The bromide ($Br^-$) component of the catalyst is preferably in the form of hydrogen bromide. The phenylterephthalic acid product may be purified by extraction, precipitation, or recrystallization procedures. Purification can also be achieved by converting the phenylterephthalic acid to an ester such as the methyl or ethyl ester followed by suitable distillation, extraction, precipitation, or recrystallization procedures.

As a further aspect of the present invention, there is provided the above step (c) by a catalyzed autoxidation of dimethyl biphenyl (DMB) to phenylterephalic acid, preferably in acetic acid solution. Five parameters were found to be important to give a good yield of high quality product and to lessen and/or eliminate the formation of byproducts such as the fluorenone (A below) and the lactone (B below). The concentration of DMB will preferably range from 0.01 M to 0.30 M, with the most preferred range being 0.05 M to 0.15 M. The catalysts are preferably cobalt and manganese and the cocatalyst is bromine in any ionic or potentially ionic form. The concentration of Co preferably ranges from 0.015 M to 0.06 M, with the most preferred range being 0.025 M to 0.035 M; the concentration of Mn preferably ranges from 0.0 to 0.07 M, with the most preferred range being 0.002 M to 0.006 M. The concentration of bromine preferably ranges from 0.010 M to 0.139 M, with the most preferred range being 0.060 M to 0.080 M. The temperature of the oxidation should be maintained in the range of 80° C. to 190° C., with the preferred range being 100° C. to 120° C. The concentration of O₂ in the solution the oxidation is taking place in is critical to the success of the process. Any means which can facilitate the diffusion of O₂ through the solution, that is, the mass transfer of O₂ from the gas phase through the liquid of solution and to the radical interemdiates, is desirable. Under these conditions which are outlined in the experimental section, the oxidation was carried out at conditions where the concentration of O₂ in the off-gas was maintained in the range of 1% to 12%, with the preferred range being 8% to 12%. The concentration of water in the oxidation is maintained in the range of 1.4 M to 5.5 M, with the preferred range being 2.0 M to 3.0 M.

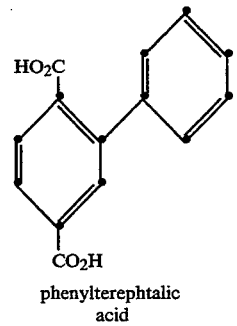

phenylterephtalic acid

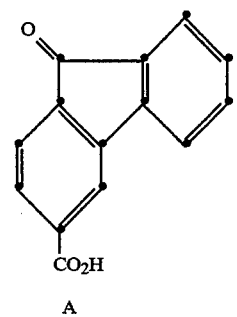

A

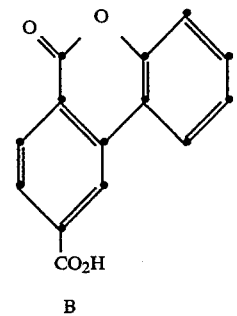

B

As a further preferred embodiment of the present invention, there is provided the above process, further comprising the step of separating 2-phenylterephthalic acid from by-products of the formulae

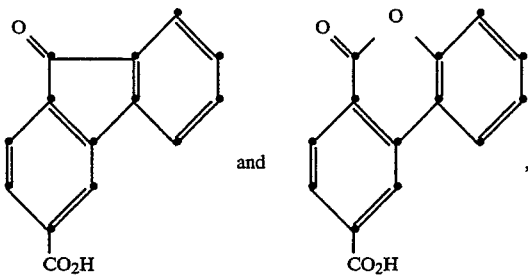

and which comprises treating crude reaction product with an aqueous alkali metal salt, followed by filtration to provide an aqueous filtrate, and acidification of said filtrate to a pH of about 2.5-3.0, followed by isolation of solid phenylterephthalic acid.

Experimental Section

Example 1 - Preparation of Cyclohexyl-p-Xylene p-Xylene (50 g, 0.47 moles), 2 g (0.024 moles) of cyclohexene and 1 g of Y-20 zeolite catalyst were placed in a 100 Ml, 3-neck flask bottle with a stirrer and water condenser. The flask was purged with nitrogen and the reaction mixture heated until refluxing began at 126° C.. Cyclohexene was added in 2 g increments and the reflux temperature gradually increased to 141° C. A total of 12 g of cyclohexene was added during a total reaction time of 7 hours.

Several samples were taken during the course of the reaction. The results of G.C. analyses on these samples is as follows. Concentrations of the components are expressed in area %.

| Sample Min. | Cyclohexene | p-Xylene | Cyclohexyl-p-Xylene | Docyclohexyl-p-Xylene |
| --- | --- | --- | --- | --- |
| 20 | Trace | 90.3 | 8.4 | 0.4 |
| 60 | Trace | 81.6 | 16.8 | 1.2 |
| 90 | Trace | 74.5 | 22.6 | 1.9 |
| 130 | 0.1 | 63.4 | 30.6 | 5.1 |
| 300 | 3.3 | 54.3 | 34.1 | 6.4 |
| 420 | 1.9 | 54.4 | 35.0 | 6.7 |

Example 2 - Preparation of Cyclohexyl-p-Xylene p-Xylene (3 kg, 28.3 moles) were added to a 12 13-neck flask. With stirring, 40 g of AlCl3 were added to the flask. The flask was cooled externally with an ice bath and the temperature of the reaction mixture decreased to 12° C. Cyclohexene was added to the reaction mixture from a dropping funnel at a rate which was constantly adjusted to maintain the reaction temperature in the range of 20 to 25° C. A total of 1400 mL (1135 g, 13.8 moles) of cyclohexene was added during the 90 minute reaction period. A total of 500 mL of water was added with stirring to deactivate the AlCl3 catalyst. The aqueous layer was separated from the organic layer and then the organic layer was washed two more times with 1 L portions of water. After removing the water layer, 40 g of anhydrous CaCl2 was added with stirring to dry the organic layer. After 15 minutes stirring, the organic layer containing the cyclohexyl-p-xylene was decanted from the calcium chloride. Assay of the crude reaction mixture by gas chromatograph showed it to contain 67.1 percent p-xylene, 26.1 percent cyclohexyl-p-xylene and 6.1 percent dicyclohexyl-p-xylene.

The reaction mixture was distilled through a 1-inch diameter glass column containing 22 inches of Goodloe packing. Solvent and low boiling impurities were stripped off and a small forecut is taken before collecting 982 g of cyclohexyl-p-xylene at 200° C./120 torr.

Example 3 - Dehydrogenation of cyclohexyl-p-Xylene

To a 3-liter three neck flask fitted with a stirrer, Vigeux column (1 inch X 12 inches), condenser, and distillation head was added 90.2 g (wet weight, 53% water) of 5 % sulfided Pd/C (Calsicat E-180) catalyst and 610 g of n-propanol. The reaction mixture was heated to reflux (base temperature 111° C.) and the water/n-propanol azeotrope removed at a head temperature of 95° C. After all water was removed from the system, the reaction mixture was cooled to less than 100° C. and 420.3 g (2.23 moles) of cyclohexyl-p-xylene were added. Cold water to the condenser was stopped and 15 psi steam was passed through the condenser. The reaction mixture was heated by means of a heating mantle until the base temperature was 246° C. (head temperature was at 209° C.). The reaction was continued for 4.25 hours with the base temperature gradually increasing to 272° C. and the head temperature up to 254° C. Samples removed from the reaction mixture at selected times were analyzed by gas chromatography and the results summarized below:

| Reaction Time, Min. | Base Temp. °C. | Head Temp. °C. | Conversion to phenyl-p-xylene, % |
|---|---|---|---|
| 75 | 266 | 215 | 50 |
| 150 | 269 | 245 | 75 |
| 210 | 272 | 254 | 92 |
| 255 | 272 | 254 | 97.6 |

The heating mantle was removed and steam removed from the condenser and the reaction mixture was allowed to cool to room temperature under a nitrogen atmosphere.

The reaction mixture was filtered to remove catalyst and then distilled through a 1-inch diameter column containing 22 inches of Goodloe packing. After removing solvent and low boiling impurities, 362.7 g of product (2,5-dimethylbiphenyl) was collected at 140° C./14.5 torr.

Example 4 - Oxidation of 2,5-Dimethylbiphenyl

Into a 2 liter Hastelloy autoclave were placed 1000 mL of 95% acetic acid, 60 g (0.33 moles) of 2,5-dimethylbiphenyl, 8.0 g of cobalt acetate tetrahydrate, 0.8 g of manganese acetate, 12.0 g of 48% hydrogen bromide, and 50 mL of water. The reaction vessel was sealed, heated to 100° C. and pressured to 200 psig with air while the reaction mixture was being stirred. Air was continually fed to the autoclave at such a rate that 7-8% oxygen was maintained in the off gas stream which was continually removed. The reaction was maintained under these conditions for 5 hours. Analysis of the reaction product by liquid chromatography indicated 92% yield of phenyl terephthalic acid.

Example 5

2,5-Dimethylbiphenyl (60 g; 0.3 mole) was dissolved in 100 g of acetic acid to give a feed solution which was added to the reaction mixture over a period of 3 hr. The reaction was carried out in a two-liter stirred autoclave which can be operated at pressures from 25 to 350 psig and temperatures from 50° C. to 200° C. and is agitated by a magnetic stirrer equipped with a Rushton turbine. The autoclave was equipped with a dip tube which allowed the reaction mixture to be sampled periodically while the reaction was taking place. The mixture was stirred at 990 rpms while air was passed through the mixture at a rate of 5 slm with a head pressure of 300 psig. The autoclave was initially charged with a catalyst mixture composed of cobaltous acetate tetrahydrate (8.0 g; 0.032 moles), manganous acetate (0.8 g; 0.0037 moles), hydrogen bromide (48% solution) (12.0 g; 0,071 moles), water (50 g; 2.8 moles), and acetic acid (900 g). The autoclave was heated to 100° C. with stirring and air flow. The reaction was initiated by the addition of a small amount of peracetic acid in order to give consistent results from one experiment to another. The reaction was begun by the addition of the feed solution. The reaction mixture was sampled periodically and analyzed by liquid chromatography to determine the amount of $\phi$TPA, flourenone 1, and lactone 2. The final product mixture was sampled while hot before any product had crystallized in order to obtain a representative sample. In this example, the yield of $\phi$TPA was 90-91%, the yield of 1 was 0%, and the yield of 2 was 9-10%.

Examples 6 through 14

The table below illustrates the effect of temperature, catalyst concentration, water concentration, and $O_2$ concentration.

| Ex. | Temp. °C. | [Co] | [Mn] | [Br] | $H_2O$ | min. [$O_2$] | % $\phi$TPA | % 1 | % 2 |
|---|---|---|---|---|---|---|---|---|---|
| 5 | 100 | .03 | .0035 | .07 | 2.8 | 5.7 | 91 | 0 | 9 |
| 6 | 130 | .03 | .0035 | .07 | 2.7 | 4.6 | 85 | 4 | 11 |
| 7 | 100 | .06 | .0070 | .139 | 2.7 | 1.9 | 87 | 8 | 5 |
| 8 | 100 | .015 | .0018 | .035 | 2.7 | 8.6 | 89 | 0 | 11 |
| 9 | 100 | .03 | .0035 | .07 | 2.7 | 2.2 | 84 | 8 | 8 |
| 10 | 100 | .03 | .0035 | .07 | 1.4 | 7.9 | 89 | 0 | 11 |
| 11 | 100 | .03 | .0035 | .07 | 5.5 | 8.6 | 92 | 3 | 5 |
| 12 | 100 | .03 | 0 | .07 | 2.7 | 5.4 | 87 | 1 | 11 |
| 13 | 100 | .03 | .035 | .07 | 2.7 | 6.8 | 91 | 4 | 5 |
| 14 | 100 | .025 | .03 | .062 | 2.4 | 9.0 | 92 | 0 | 8 |

Example 15 - Purification Method for Crude Phenylterephthalic Acid

A crude 4 g sample of phenylterephthalic acid is treated with 50 ml of a 10% potassium acetate solution and warmed to 25° C. The resulting slurry is filtered and the filtrate acidified to about pH was <3. The purified product precipitates out of this solution.

We claim:

1. A process for preparing a compound of Formula (1),

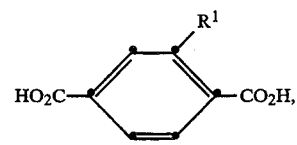

wherein $R^1$ is phenyl, which comprises the steps
(a) alkylating a compound of the formula

with cyclohexene in the presence of an acid catalyst to provide a compound of Formula (2),

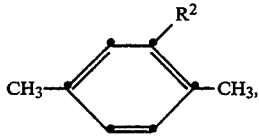

wherein R² is cyclohexyl; followed by (b) dehydrogenation; and (c) oxidation in the presence of air or oxygen and a cobaltous bromide oxidation catalyst system, at a temperature of about 75° C. to 250° C., and at a pressure of about 10 to 1000 psig wherein the concentration of reaction off-gas oxygen is maintained in the range of 1% to 12%.

2. The process of claim 1, wherein Cobalt is in the form of a salt selected from the group consisting of cobalt acetate, cobalt propionate, cobalt butyrate, cobalt benzoate, and cobalt toluate.

3. The process of claim 1, wherein the oxidation catalyst system further comprises manganese or zirconium.

4. The process of claim 3, wherein the manganese is in the form of salt selected from the group consisting of manganese acetate, manganese propionate, manganese butyrate, manganese benzoate, and manganese toluate.

5. The process of claim 3, wherein the zirconium is in the form of a salt selected from zirconium acetate, zirconium propionate, zirconium butyrate, zirconium benzoate, and zirconium toluate.

6. The process of claim 1, further comprising the step of separating 2-phenylterephthalic acid from by-products of the formulae

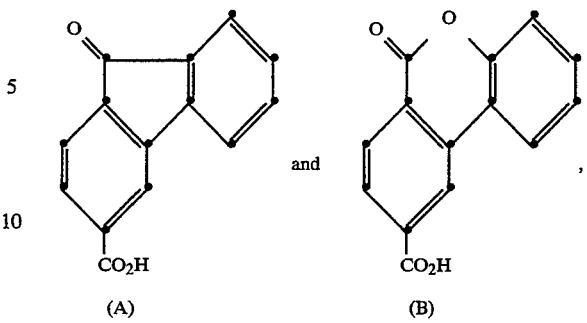

which comprises treating crude reaction product with an aqueous alkali metal salt, followed by filtration to provide an aqueous filtrate, and acidification of said filtrate to pH of about 2.5-3.0, followed by isolation of solid product of formula 1.

7. A process for preparing 2-phenylterephthalic acid which comprises oxidizing in a reaction mixture a compound of the formula

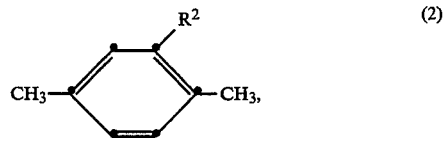

wherein R² is phenyl, in the presence of air or oxygen and a cobaltous bromide oxidation catalyst system, at a temperature of about 75° C. to 250° C., and at a pressure of about 10 to 1000 psig wherein the concentration of reaction off-gas oxygen is maintained in the range of 1% to 12%.

8. The process of claim 7, wherein cobalt is in the form of a salt selected from the group consisting of cobalt acetate, cobalt propionate, cobalt butyrate, cobalt benzoate, and cobalt toluate.

9. The process of claim 8, wherein the oxidation catalyst system further comprises manganese or zirconium.

10. The process of claim 10, wherein the manganese is in the form of a salt selected from the group consisting of manganese acetate, manganeses propionate, manganese butyrate, manganese benzoate, and manganese toluate.

11. The process of claim 10, wherein the zirconium is in the form of a salt selected from the group consisting of zirconium acetate, zirconium propionate, zirconium butyrate, zirconium benzoate, and zirconium toluate.

12. The process of claim 7, wherein the process is carried out in acetic acid solution containing water, wherein the concentration of Cobalt is about 0.015M to 0.06M; the concentration of manganese is about 0.002M to 0.006M; the concentration of the 0: in the reaction off-gas is maintained at from about 7% to 12%; the concentration of water in the reaction mixture is about 1.4 M to 5.5 M; the concentration of bromide ion is 0.010 M to 0.139 M, and the temperature is from about 80° C. to 190° C.

* * * * *